United States Patent [19]

Romine et al.

[11] Patent Number: 5,597,851
[45] Date of Patent: Jan. 28, 1997

[54] METHOD FOR THE ADDITION OF VULCANIZED WASTE RUBBER TO VIRGIN RUBBER PRODUCTS

[75] Inventors: Robert A. Romine, Pasco; Lesley J. Snowden-Swan, Benton City, both of Wash.

[73] Assignee: Battelle Memorial Institute, Richland, Wash.

[21] Appl. No.: 528,076

[22] Filed: Sep. 14, 1995

[51] Int. Cl.$^6$ ................................ C12M 1/10; C12R 1/07
[52] U.S. Cl. ................................ 521/41; 521/45; 435/130; 435/166; 435/167; 435/262
[58] Field of Search ...................................... 435/130, 166, 435/167, 262; 521/41, 45

[56] References Cited

U.S. PATENT DOCUMENTS 5,275,948 1/1994 Straube et al. ........................... 435/262
5,344,778 9/1994 Kilbane, II ............................... 435/262

*Primary Examiner*—Frederick Krass
*Attorney, Agent, or Firm*—Paul W. Zimmerman

[57] ABSTRACT

The invention is a method of using enzymes from thiophyllic microbes for selectively breaking the sulfur rubber cross-link bonds in vulcanized rubber. The process is halted at the sulfoxide or sulfone step so that a devulcanized layer is reactive with virgin rubber.

20 Claims, 4 Drawing Sheets

METHOD FOR THE ADDITION OF VULCANIZED WASTE RUBBER TO VIRGIN RUBBER PRODUCTS

This invention was made with Government support under Contract DE-AC06-76RLO 1830 awarded by the U.S. Department of Energy. The Government has certain rights in the invention.

FIELD OF THE INVENTION

The present invention is a method of selectively breaking the sulfur rubber cross-link bonds (devulcanizing) in vulcanized rubber, thereby permitting scrap or used rubber articles to be recycled into a virgin rubber batch. More specifically, the present invention is a method of devulcanizing rubber using microbes or the enzymes expressed by the microbes.

BACKGROUND OF THE INVENTION

Vulcanized rubber is one of the most voluminous and serious waste product sources in the United States. For example, in 1990 approximately 3 billion waste tires existed in the United States alone, and about 250,000,000 more tires are added every year. This makes waste tires one of the most significant environmental and waste storage problems. In addition to environmental concerns, the waste tires pose significant fire and safety problems for those that live in the vicinity of these stockpiles.

Currently, less than 13% of the waste tires generated annually are recycled by any means. The principal methods now in use are tire derived fuel (TDF), pyrolysis for recovering starting materials, rubber modified asphalt pavements and reduction by grinding and cryofracturing for reincorporation into low-performance moldable products (gaskets, athletic track surfaces). An example of a process combining devulcanized rubber with a thermoplastic is U.S. Pat. No. 5,359,007 to Luiz C. Olivera Da Cunha Lima.

Because vulcanized rubber is chemically stable, it is difficult to combine it into new material because bonding between the new material and the vulcanized rubber is weak. Present methods of devulcanization are costly, hence there is a need for a cost effective de-vulcanization process.

Currently, only about 3 to 4 percent by weight of reclaimed rubber can be used in the manufacture of new tires. In this process, the waste tires are ground into a powder, then rinsed (sometimes with hazardous chemicals) and dried, and then mixed within a virgin rubber matrix. The limitation of this process is the low percentage by weight of waste rubber that can be re-used.

Vulcanization

Useful rubber products cannot be manufactured without vulcanization. Unvulcanized rubber is generally weak and undergoes permanent deformation after a large strain is imparted on the article. Conversely, vulcanized rubber forcibly retracts to approximately original shape after a large mechanically imposed deformation. Vulcanization can be defined as a process which increases the retractile force and reduces the amount of permanent deformation remaining after the removal of the deforming force (Mark 1994) and consists of using sulfur compounds to bind the rubber molecules together.

Vulcanization is more particularly described as the process of chemically producing network junctures by the insertion of crosslinks between polymer chains. Sulfur is one of the most common crosslink agents used in the manufacture of tires. The addition of a small amount of sulfur (typically 1–2.5%) in a tire rubber compound is responsible for the majority of the physical properties of the final product, specifically, strength, elasticity, resistance to degradation, and durability. However, these benefits prove to be a major problem when attempting to recycle or re-use vulcanized rubber. The strength of the cross-link bonds created by the vulcanization process prevents the vulcanized rubber from melting, binding within a virgin rubber matrix, or dissolving in solvents.

Hence, there is a need for a method of devulcanization that would permit a substantially greater portion of scrap or waste vulcanized rubber to be re-used.

SUMMARY OF THE INVENTION

The present invention is a method for selectively breaking the sulfur cross-link bonds in vulcanized rubber with at least one enzyme. Further, the present invention is a method of breaking the sulfur cross-link bonds on the surface of a rubber article or particle leaving a core of the article or particle vulcanized. The method of the present invention further includes the step of halting the devulcanization reaction at the sulfoxide or sulfone step.

An advantage of the method of the present invention is that the enzymatic devulcanization of rubber article surfaces is performed at ambient to moderate temperatures, one atmosphere of pressure, and uses no hazardous compounds or toxic chemicals. Additionally, many of the components used in the process can be recycled.

Therefore, it is the object of the present invention to provide a method of devulcanization that permits a greater portion of scrap and waste vulcanized rubber to be re-used.

The subject matter of the present invention is particularly pointed out and distinctly claimed in the concluding portion of this specification. However, both the organization and method of operation, together with further advantages and objects thereof, may best be understood by reference to the following description taken in connection with accompanying drawings wherein like reference characters refer to like elements.

DESCRIPTION OF THE PREFERRED EMBODIMENT(S)

The method of the present invention has the steps of exposing a surface of a vulcanized rubber article to at least one enzyme, maintaining the exposure for a time sufficient to convert sulfur to sulfoxide or sulfone, and halting conversion and preventing further degradation of the sulfoxide or sulfone. It is important to halt the conversion upon production of sulfoxide or sulfone because these are reactive and therefore bondable with virgin rubber, whereas the reactive downstream R—OSO$_2$—R or sulfate is non reactive with virgin rubber.

Figure 1:
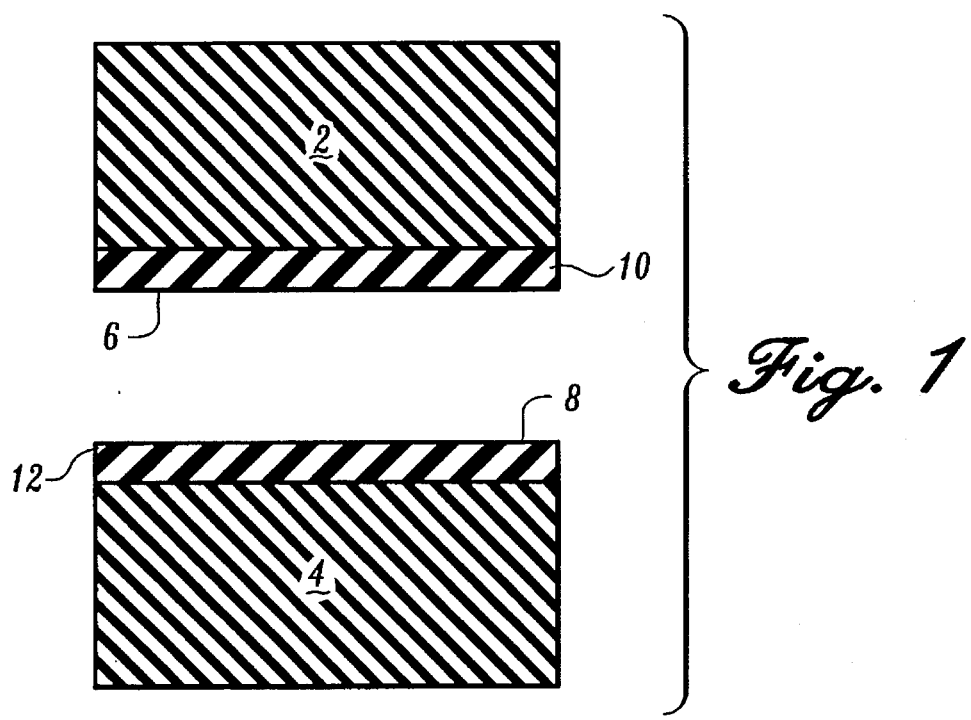
FIG. 1 is a cross section of a pair of rubber articles having devulcanized layers.

An article of vulcanized rubber is shown in FIG. 1. A first piece 2 and a second piece 4, both of vulcanized rubber, have been exposed to an enzyme according to the method of the present invention to create devulcanized layers 10 and 12. The first and second pieces 2 and 4 may be joined at surfaces 6 and 8. The joining of the pieces 2 and 4 (also referred to as scrap pieces, or vulcanized scrap rubber pieces) may be done by placing them in direct contact with each other and applying pressure and heat. The reformation of the sulfur cross-link bonds in the devulcanized layers 10 and 12 and across the surfaces 6 and 8 causes the two pieces 2 and 4 of rubber to be joined. Either two pieces can be joined in this manner, or, if desired, a multiplicity of pieces can be joined to form a matrix of scrap pieces of waste vulcanized rubber.

Figure 2:
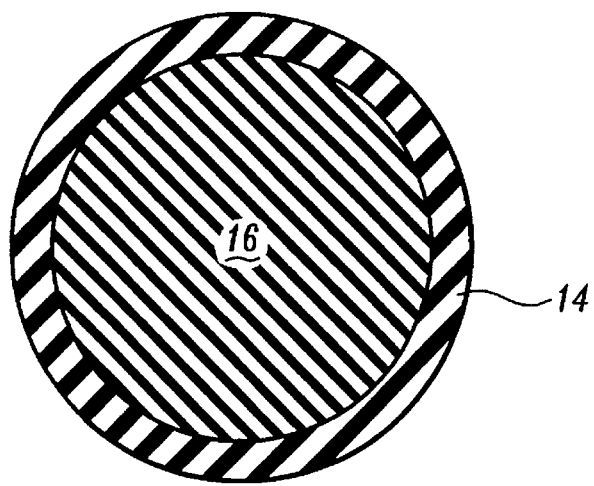
FIG. 2 is a cross section of a rubber particle having a devulcanized layer.

Another article of vulcanized rubber is shown in FIG. 2 in the shape of a sphere or spheroid. An outer surface layer 14 has been devulcanized by the method of the present invention leaving a vulcanized core 16. The article may be incorporated into a virgin rubber matrix and bonded thereto by the outer surface layer 14.

In a preferred embodiment of the present invention vulcanized rubber item, for example a tire, is first ground to a fine mesh to form a plurality of particles. It is preferred that the particles are less or equal to about 75 microns (200 mesh) in diameter. The small size particles provide more surface area for the enzyme devulcanization for a given weight of waste material. The powder is then exposed to at least one enzyme. In one embodiment, the enzyme is produced by a microbe organism in a bio-reactor. The particles may be placed with a population of microbes for exposure to the enzyme for a time sufficient to permit devulcanization of particle surfaces. When the required time has elapsed, devulcanization is halted and the resulting powder is rinsed and dried before being added to a virgin rubber matrix.

Microbes that have been identified as producing an enzyme useful for making a devulcanized layer on a vulcanized rubber particle are thiophyllic microbes. More specifically, thiophyllic microbes include *Thiobacillus ferrooxidans*, *T. thiooxidans*, *Rhodococcus rhodochrous*, and *Sulfolobus acidocaldarius*. Microbes and enzymes they produce are sensitive to temperature. Specifically, microbes decrease activity with decreasing temperature and do not survive high temperatures. Accordingly, it is preferred that when microbes are present, the temperature is maintained at a microbial "comfortable" range within operative limits of from above the freezing temperature of water to below the boiling temperature of water at an atmosphere of pressure. More specifically, it is preferred to avoid the need for dedicated heating or cooling equipment by permitting devulcanization at ambient temperature. Where devulcanization is carried out within a building, the temperature internal to the building would prevail as long at the temperature is held within the operative limits described above. It is most preferred to conduct microbe devulcanization at a temperature from about 20° C. to about 32° C.

Where an enzyme is produced separately and then applied to the rubber article separately from the microbe(s), the temperature is limited by the chemical activity of the enzyme. Again, however, it is preferred to avoid the use of dedicated heating or cooling equipment so temperatures as described above are useful for enzymatic devulcanization.

Devulcanization is halted upon conversion of the sulfur bonds to sulfoxide (R—SO—R) or sulfone (R—SO$_2$—R), which are reactive with virgin rubber. Further reaction to (R—OSO2—R), or ultimately to sulfate (SO$_4$), is undesirable because the devulcanized surface is unreactive. If the process is stopped at the sulfoxide or the sulfone step, then the powder will be reactive with the virgin rubber matrix.

To determine when to stop the reaction, samples may be drawn from the bioreactor and analyzed by infrared spectroscopic analysis. Results of this analysis indicate that the bioreactor step requires a time from about one to about three days (at least about 24 hours), with about three days permitting a sufficient amount of sulfone, while avoiding further reaction. The conversion is halted by removing the particles from the enzyme(s) and rinsing to remove any remaining microbes or enzymes or other waste products. The powder is then dried.

After the devulcanized powder is dried, it may be introduced into a virgin rubber batch. A further step of homogenizing comprises adding a compound selected from the group consisting of resins, vulcanizers, oils, accelerators, retarders, pigments, dyes, dispersants, or a mixture thereof. Alternatively, the dried devulcanized powder may be added to a thermoplastic, for example styrene, acrylics, cellulosic, polyethylenes, vinyls, nylons, or fluorocarbons. About 10 to about 20 wt % of devulcanized powder can be added to virgin rubber matrix. It should be noted that this is 3 to 4 times the current capability of the methods in the art. Positive experimental results have been shown at 15% composition of recycled material by weight of the finished product.

An added advantage is that revulcanization is not required. However, depending upon the amount of waste rubber particles that were added, further vulcanization can be beneficial.

EXAMPLE 1

An experiment was conducted to compare infrared spectra of vulcanized rubber particles having been devulcanized by the method of the present invention, to vulcanized rubber particles that had not been devulcanized.

Bacterial strains used in the experiment were *Thiobacillus ferrooxidans*, *Thiobacillus thiooxidans*, *Rhodococcus rhodochrous-IGTS8*, *Sulfolobus acidocaldarius*, and an unidentified bacteria from the American Type Culture Collection (ATCC).

Fourier Transform Infrared Spectroscopy Data

Figure 3A:
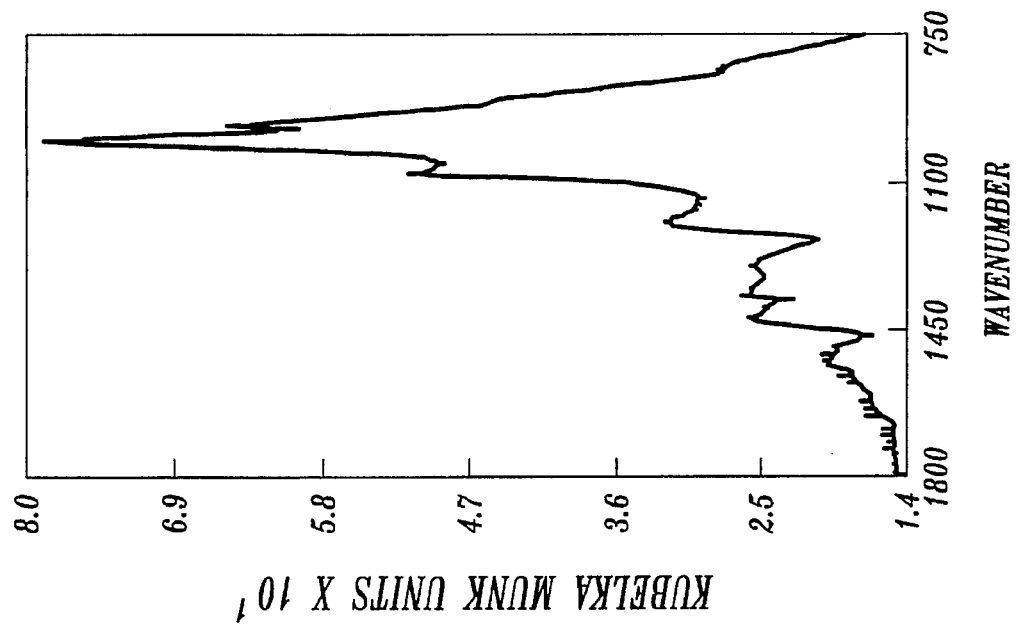
FIG. 3a is an illustration of the infrared (IR) spectra of surface ground tire rubber that was acted upon by the bacteria *S. acidocaldarius*.
Figure 3B:
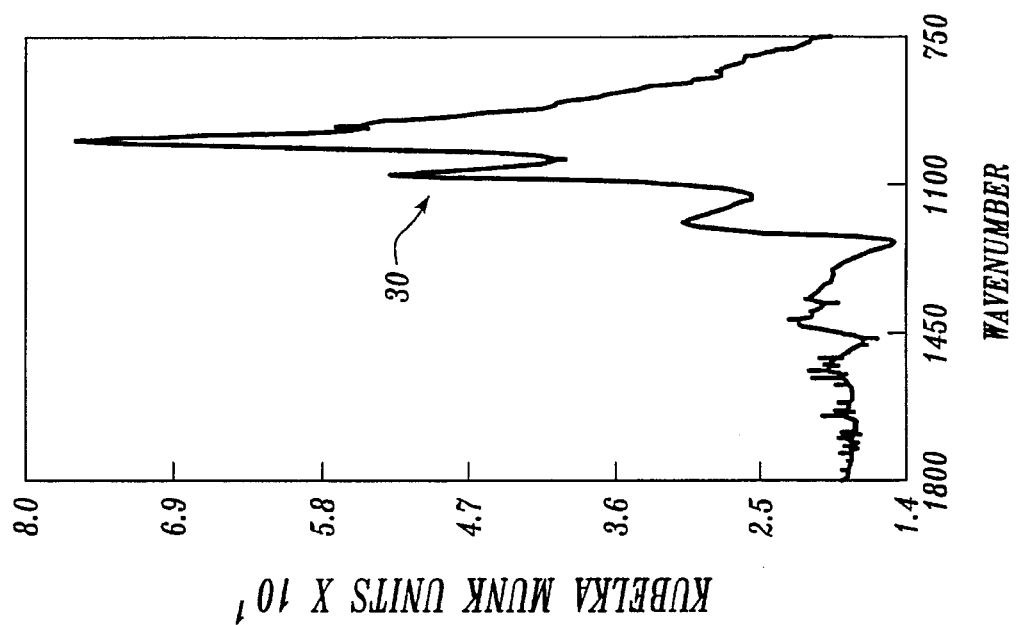
FIG. 3b is an illustration of the IR spectra of ground tire rubber that not been acted upon by bacteria or enzymes.

Results are shown in FIG. 3*a* for rubber particles devulcanized by bioprocessing with *S. acidocaldarius* for 72 hours, and FIG. 3*b* for non-processed rubber particles. The non-processed rubber particles were subjected to all identical conditions as were the bioprocessed rubber particles, but in the absence of bacterium, *S. acidocaldarius* control. These spectra show a new absorbance peak 30 at 1032 cm$^{-1}$ indicating that a transformation has occurred to the surface of the rubber in the region that is typically assigned to sulfur-oxygen bonding. This absorbance is not present in the control. The absorbance peak 30 was strongest for bacteria/enzyme exposure of 2 to 3 days. Beyond a 3-day exposure, the absorbance peak 30 diminishes and finally disappears. The absorbance peak 30 is not present in spectra obtained on rubber samples biotreated for seven (7) days.

XANES Experimental Data

Figure 4A:
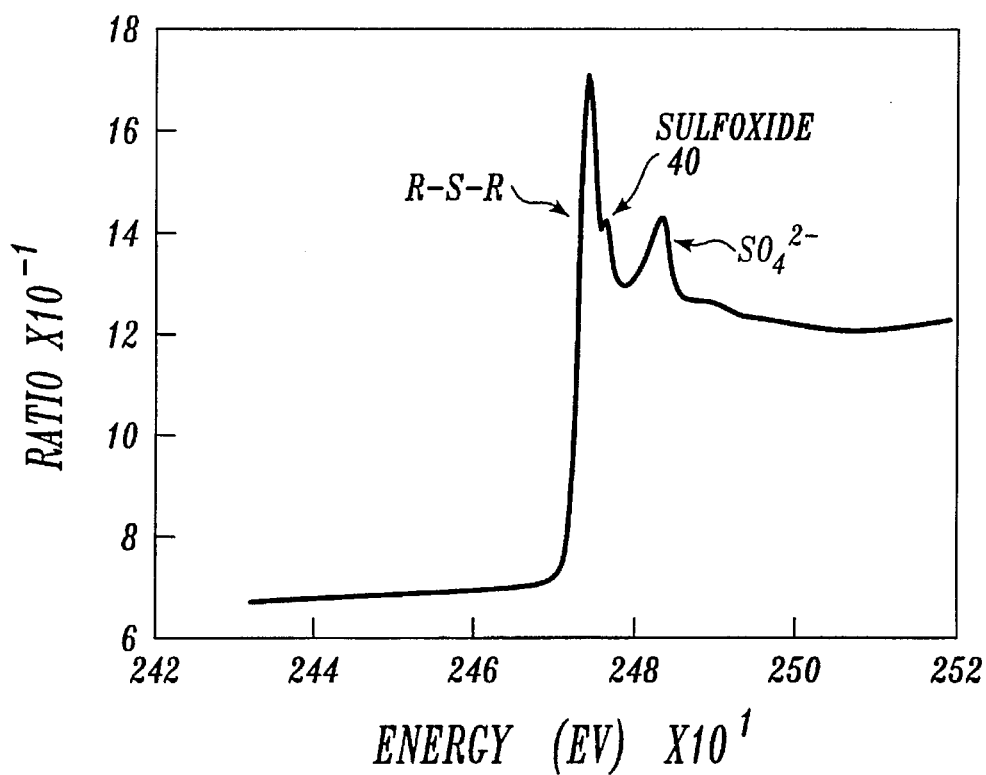
FIG. 4a is a graphical representation of the XANES data from a treated rubber sample.
Figure 4B:
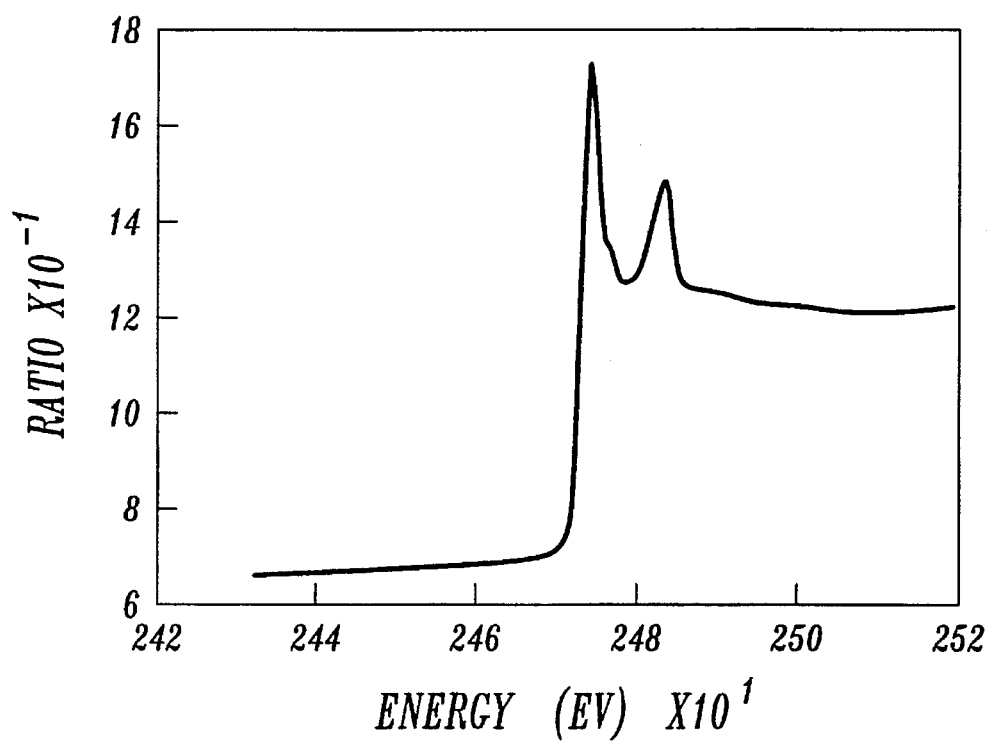
FIG. 4b is a graphical representation of the XANES data from a rubber sample that has not been treated.

X-Ray Analysis of Near Edge Surfaces (XANES) analysis was performed on ground tire rubber (GTR) samples. XANES is an excellent technique for characterizing the oxidation state of sulfur in solids. Results illustrated in FIGS. 4a and 4b are for samples from the same bioprocess batches used above. Results show that surface sulfur is oxidized to higher oxidation states during bioprocessing, as predicted by the degradative pathway. These XANES results confirmed the expected surface chemical reactions. The new peak 40 of the XANES analysis shows a higher concentration of a partially oxidized sulfur species (sulfoxide or sulfone) and confirms the identification of new peak 30 in the IR Spectra data.

EXAMPLE 2

An experiment was conducted to compare mechanical properties of samples of vulcanized rubber made with and without devulcanized particles made by the method of the present invention. Particles were bioprocessed for 72 hours.

Figure 5:
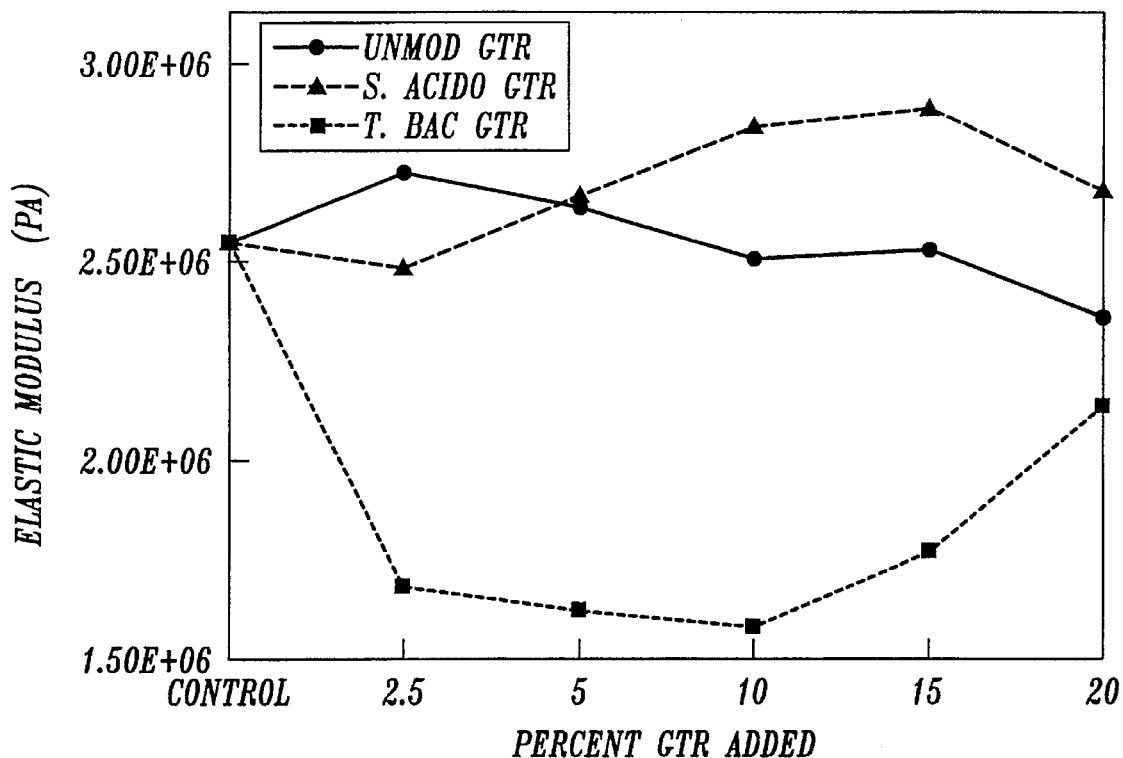
FIG. 5 is a graphical representation of elastic modulus data that illustrates the increase in elasticity due to the addition of 72-hour treated rubber to a virgin matrix.

Results are shown in FIG. 5. Rubber samples were made with base rubber with varying amounts of bioprocessed rubber particles. The "Unmodified GTR" is a set of samples made with varying amounts of non-bioprocessed rubber particles. Each sample was tested for elastic modulus.

The modulus of elasticity for samples made with particles bioprocessed with *S. acidocaldarius* exhibited an unexpected increase of 15% at a 15% loading of bioprocessed rubber particles.

The rubber samples loaded with rubber particles bioprocessed with mixed Thiobacillus exhibited poor modulus of elasticity. The mixed Thiobacillus was not as effective as *S. acidocaldarius* in biodegrading sulfur. This behavior has not been fully characterized.

Figure 6:
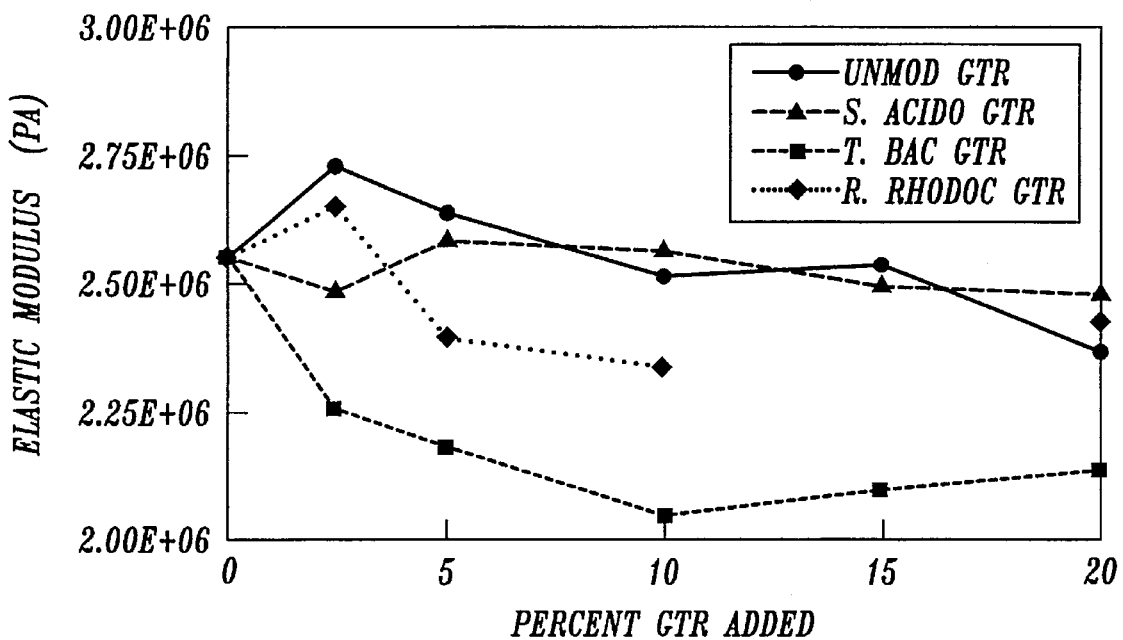
FIG. 6 is a graph of elastic modulus data showing lack of strength increase for addition of 168-hour treated rubber to a virgin matrix.

FIG. 6 shows results using particles bioprocessed for 168 hours. For *S. acidocaldarius*, the improvement observed for 72 hour processing is lost, and the modulus of elasticity of the loaded samples is very nearly that of samples using untreated rubber particles. Thiobacillus showed an improvement over its 72 hour processing, but is still poor, and *R. rhodochrous* processed for 162 hours behaved about the same as unmodified rubber particles.

OTHER EMBODIMENTS

While a preferred embodiment of the present invention has been shown and described, it will be apparent to those skilled in the art that many changes and modifications may be made without departing from the invention in its broader aspects. The appended claims are, therefore, intended to cover all such changes and modifications as fall within the true spirit and scope of the invention.

We claim:

1. A method for modifying a surface layer of a vulcanized rubber article, comprising the steps of:
    (a) placing said vulcanized rubber article in contact with at least one thiophyllic microbe;
    (b) converting sulfur in said surface layer of the vulcanized rubber article to sulfoxide or sulfone; and
    (c) halting the converting (step (b)) to prevent further reaction of the sulfur to a sulfur compound that is non-reactive with virgin rubber; wherein
    (d) said surface layer is devulcanized and contains partially oxidized sulfur, said surface layer remaining on a vulcanized core.

2. The method as recited in claim 1, wherein said thiophyllic microbe is selected from the group consisting of *Thiobacillus ferrooxidans*, *T. thiooxidans*, *Rhodococcus rhodochrous*, and *Sulfolobus acidocaldarius*.

3. The method as recited in claim 1, wherein said converting is done at a temperature of from about 20° C. to about 32° C.

4. The method as recited in claim 3, wherein said converting is done for a time of at least 24 hours.

5. The method as recited in claim 1, wherein said vulcanized rubber article is at least one particle.

6. The method as recited in claim 5, wherein said particle(s) is/are obtained from grinding a vulcanized rubber item.

7. The method as recited in claim 6, wherein said vulcanized rubber item is a tire.

8. The method as recited in claim 1, wherein the step of halting comprises the step of:
    rinsing the article with water and removing the thiophyllic microbe(s).

9. A method for modifying a surface layer of a vulcanized rubber article comprising the steps of:
    (a) placing said vulcanized article in contact with at least one enzyme from a thiophyllic microbe;
    (b) converting, with said enzyme(s), sulfur in said surface layer of the vulcanized rubber article to sulfoxide or sulfone; and
    (c) halting the converting (step (b)) to prevent further reaction of the sulfur to a sulfur compound that is non-reactive with virgin rubber; wherein
    (d) said article has said surface layer devulcanized and contains partially oxidized sulfur, said surface layer remaining upon a vulcanized core.

10. The method as recited in claim 9, wherein said thiophyllic microbe is selected from the group consisting of *Thiobacillus ferrooxidans*, *T. thiooxidans*, *Rhodococcus rhodochrous*, and *Sulfolobus acidocaldarius*.

11. The method as recited in claim 9, wherein said converting is done at a temperature of from about 20° C. to about 32° C.

12. The method as recited in claim 11, wherein said converting is done for a time of at least 24 hours.

13. The method as recited in claim 9, wherein said article having said devulcanized surface layer on a vulcanized core is added to virgin rubber the weight ratio of the amount of the devulcanized article to a total amount of the devulcanized article and virgin rubber comprises up to about 20 wt %.

14. The method as recited in claim 9, wherein said vulcanized rubber article is at least one particle.

15. The method as recited in claim 14, wherein said particle(s) is/are obtained from grinding a vulcanized rubber item.

16. The method as recited in claim 15, wherein said vulcanized rubber item is a tire.

17. The method as recited in claim 9, wherein the step of halting comprises the step of:
    rinsing the article with water and removing the enzyme(s).

18. The method as recited in claim 1, wherein said thiophyllic microbe is *Sulfolobus acidocaldarius*.

19. The method as recited in claim 9, wherein said thiophyllic microbe is *Sulfolobus acidocaldarius*.

20. A method for combining scrap vulcanized rubber with virgin rubber, comprising the steps of:

(a) grinding said vulcanized rubber into particles;

(b) exposing said particles to at least one enzyme from *Sulfolobus acidocaldarius*;

(c) converting sulfur in a surface layer of each of the particles to sulfoxide or sulfone;

(d) halting the converting (step (c)) to prevent reaction of the sulfur to a sulfur compound that is non-reactive with virgin rubber; wherein (d) said surface layer is devulcanized remaining on a vulcanized core; and (e) combining the particles having said devulcanized layer with virgin rubber and forming sulfur cross-link bonds between the devulcanized layer and the virgin rubber.

* * * * *